United States Patent

Ueda et al.

[11] Patent Number: 6,083,428
[45] Date of Patent: Jul. 4, 2000

[54] FLAME-RETARDANT RESIN COMPOSITION

[75] Inventors: Eiji Ueda, Sodegaura; Hideo Kasahara, Yokosuka; Kazuhiro Matsubara; Tsutomu Katsumata, both of Kurashiki, all of Japan

[73] Assignee: Asahi Kasei Kogyo Kabushiki Kaisha, Osaka, Japan

[21] Appl. No.: 08/913,789

[22] PCT Filed: Mar. 6, 1996

[86] PCT No.: PCT/JP96/00535

§ 371 Date: Sep. 5, 1997

§ 102(e) Date: Sep. 5, 1997

[87] PCT Pub. No.: WO96/27600

PCT Pub. Date: Sep. 12, 1996

[30] Foreign Application Priority Data

Mar. 7, 1995 [JP] Japan ................................. 7-046777
Mar. 7, 1995 [JP] Japan ................................. 7-046778

[51] Int. Cl.[7] .............................. C09K 21/12; C08J 5/53
[52] U.S. Cl. ............................................ 252/609; 524/127
[58] Field of Search .............................. 524/127; 252/609

[56] References Cited

U.S. PATENT DOCUMENTS

| 3,761,543 | 9/1973 | Gunsher . | |
|---|---|---|---|
| 4,683,255 | 7/1987 | Sugio et al. . | |
| 5,061,745 | 10/1991 | Wittmann et al. . | |
| 5,122,556 | 6/1992 | Kambour . | |
| 5,204,394 | 4/1993 | Gosens et al. . | |
| 5,234,979 | 8/1993 | Todtemann et al. . | |
| 5,455,292 | 10/1995 | Kakegawa et al. ................. | 524/127 |
| 5,627,228 | 5/1997 | Kobayashi ........................... | 524/127 |
| 5,672,645 | 9/1997 | Eckel et al. ......................... | 524/127 |
| 5,674,924 | 10/1997 | Lee et al. ............................. | 524/127 |
| 5,833,886 | 11/1998 | Dashevsky et al. ................. | 252/609 |

FOREIGN PATENT DOCUMENTS

| 7460 | 2/1980 | European Pat. Off. . |
|---|---|---|
| 0 129 824 B1 | 1/1985 | European Pat. Off. . |
| 0 129 825 B2 | 1/1985 | European Pat. Off. . |
| 0 135 726 B1 | 4/1985 | European Pat. Off. . |
| 0 363 608 A1 | 4/1990 | European Pat. Off. . |
| 0 611 798 A1 | 8/1994 | European Pat. Off. . |
| 6184357 | 5/1994 | Japan . |

*Primary Examiner*—Philip Tucker
*Attorney, Agent, or Firm*—Pennie & Edmonds, LLP

[57] ABSTRACT

The present invention provides a flame-retardant resin composition which comprises 100 parts by weight of a thermoplastic resin (A) and 0.1 to 30 parts by weight of one or more of organic phosphorus compounds (B) represented by the following formula (1)

$$R_1-O-\overset{\overset{O}{\|}}{\underset{\underset{R_2}{|}}{P}}-O-X-O-\overset{\overset{O}{\|}}{\underset{\underset{R_3}{|}}{P}}-O-R_4 \quad (1)$$

$$\left[\phantom{R_1-O-\overset{O}{P}-O-X-O-\overset{O}{P}-O-R_4}\right]_n$$

wherein X is $$-\underset{}{\bigcirc}-\underset{\underset{CH_3}{|}}{\overset{\overset{CH_3}{|}}{C}}-\underset{}{\bigcirc}-,$$

$R_1$, $R_2$, $R_3$ and $R_4$ independently represent a phenyl group or a xylyl group with at least one being a phenyl group and at least one being a xylyl group, and n is a positive integer.

The flame-retardant resin composition of the present invention is excellent in heat resistance, impact strength in the form of thin-walled moldings and blooming-free property on the surface of articles molded therefrom.

2 Claims, No Drawings

FLAME-RETARDANT RESIN COMPOSITION

TECHNICAL FIELD

The present invention relates to a resin composition having high flame retardance and an excellent balance of flowability (moldability) and heat resistance and a process for preparing organic phosphorus compounds used as flame retardants therefor.

BACKGROUND ART

Thermoplastic resins are widely used as materials for building construction, electric and electronic parts, household electric appliances, automobiles and fibers, because they are generally light, and excellent in water resistance, chemical resistance, electrical insulation and mechanical properties and are easy to mold.

Particularly, polycarbonate resins are widely employed as materials for housings of electric appliances, electronic office equipment such as computers, word processors and the like because of their excellence in mechanical properties, heat resistance and transparency, but the housings need high flame retardance in most cases from the viewpoint of safety.

Flame retardants have conventionally been incorporated into polycarbonate resins to make them flame retardant, but the desirable polycarbonate properties such as hardness, transparency, impact strength and rigidity are inevitably impaired due to flame-retardants incorporated therein. It is necessary to reduce to the minimum the deterioration of these desirable properties JP-B-6-45747 (equivalent to U.S. Pat. No. 5,234,979) discloses a composition comprising a polycarbonate resin and a triaryl phosphate ester such as triphenyl phosphate and the like. However, the composition has not only low heat resistance but also a problem in appearance because of the migration of the triaryl phosphate ester to the surface of moldings thereof in the course of molding, i.e., blooming. JP-B-2-18336 discloses a composition comprising a polycarbonate resin and an oligomeric phosphate ester but it has reduced heat resistance due to the plasticizing effects of the oligomeric phosphate ester. Furthermore, International Patent Publication No. WO94/03535 (corresponding to U.S. Pat. No. 5,455,292) describes a specific oligomeric phosphate ester that lessens blooming, but the flame retardant and mechanical properties of the resultant compositions are not sufficient. A composition comprising a polycarbonate resin and a rubber reinforced resin, such as a rubber reinforced ABS resin or the like, is widely employed as a material for housings of electric appliances and electronic office equipment such as computers and word processors because of its excellence in mechanical properties and heat resistance, but the housings require high flame retardance in most cases from the viewpoint of safety. The impact strength of flame-retardant resins in the form of thin-walled moldings is also one of the important properties because they are frequently molded into more lightweight, thin-walled articles as electronic office equipment has become smaller and more portable with its remarkable progress.

In accordance with such demands, organic phosphorus compounds have been added to the compositions comprising the polycarbonate resins and the rubber reinforce resins such as ABS resins or the like for the purpose of imparting flame retardance thereto. For example, JP-A-2-32154 (equivalent to U.S. Pat. No. 5,061,745) discloses a composition comprising a polycarbonate resin, a rubber reinforced resin such as a rubber reinforced ABS resin or the like and a triaryl phosphate ester such as triphenyl phosphate. However, the composition has not only low heat resistance but also a problem in appearance because of the migration of the triaryl phosphate ester to the surface of moldings thereof in the course of molding, i.e., blooming. JP-A-2-115262 (equivalent to U.S. Pat. No. 5,204,394) discloses a composition comprising a polycarbonate resin, a rubber reinforced resin such as an ABS resin or the like and an oligomeric phosphate ester. However, the composition has the drawbacks of degradation in heat resistance due to the plasticizing effects of the oligomeric phosphate ester and blooming in the course of molding.

Furthermore, polyphenylene ether resins, which are excellent in mechanical properties, electrical properties, acid and alkali resistance and which are also low in water absorption and stable in dimensions, are widely used as materials for housings and chassis of electric appliances and electronic office equipment such as computers, word processors and the like. These housings require high flame retardance in most cases. The polyphenylene ether resins are excellent in flame retardance but inferior in processability, so that, in use, they are usually alloyed with styrene resins. As a result, their flame retardance deteriorates.

It has been known that a triaryl phosphate ester such as triphenyl phosphate, cresyl diphenyl phosphate, tricresyl phosphate, tris(isopropyl) phenyl phosphate and the like may be mixed as a flame retardant with the polyphenylene ether resins in order to improve their flame retardance, but the resultant polyphenylene ether resin compositions have defects such as deterioration of heat resistance and other properties and drawbacks such as volatilization, smoke emission and blooming of the incorporated phosphate ester in the course of molding.

To obviate the aforementioned defects and drawbacks, organic phosphate esters having larger molecular weight have been tried as flame retardants for practical use. For example, resorcinol tris(2,6-dimethylphenyl)phosphate is disclosed in EP-A-0007460, whereas resorcinol bis (diphenyl phosphate) of are disclosed in EP-A-0129824, EP-A-0129825, EP-A-0135726 and GB-A-2043083. Furthermore, tri(biphenyl) phosphate is disclosed in U.S. Pat. No. 4,683,255. However, these phosphate esters must be employed in large quantities for flame-retarding. According to our research findings, the resin compositions flame-retarded by incorporating these phosphate esters therein corrode molds during molding, the phosphate esters therein denature, the moldings thereof discolor and blister during molding or during a long time use and further the moldings deteriorate in electrical properties and flame retardance due to water absorption.

Thus, it has been impossible so far to provide the resin compositions which are simultaneously satisfactory in the flame retardance, performance and stability required of products. It is particularly necessary to further improve a balance of heat resistance and moldability of the flame-retardant resin compositions.

DISCLOSURE OF THE INVENTION

According to our findings, a resin composition which is difficult to bloom, which is excellent in the balance of heat resistant and flowable properties, which has an improved impact strength in the form of thin-walled moldings and which has an excellent flame retardance without sacrificing its mechanical strength, may be obtained by mixing the phosphorus compounds represented by the formula (1) with a thermoplastic resin.

Thus, present invention provides a flame-retardant resin composition which comprises 100 parts by weight of a thermoplastic resin (A) and 0.1 to 30 parts by weight, based upon 100 parts by weight of resin (A), of at least one organic phosphorus compound (B) represented by the following formula (1):

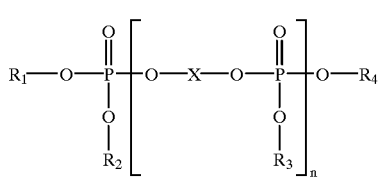
(1)

wherein X is:

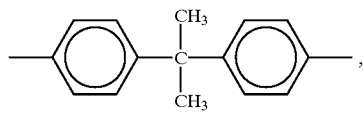

$R_1$, $R_2$, $R_3$ and $R_4$ independently represent a phenyl group or a xylyl group with at least one being a phenyl group and at least one being a xylyl group, and n is a positive integer.

Hereinafter, the present invention will be described in more detail. Thermoplastic resins which may be used as component (A) according to the present invention include polycarbonate resins, polystyrene resins, polyphenylene ether resins, acrylic resins, polyolefin resins, polyamide resins and the like. Of these, preferable are polycarbonate resins, blends of polycarbonate resins and rubber reinforced resins, polyphenylene ether resins, and blends of polyphenylene ether resins and polystyrene resins.

The polycarbonate resins of the present invention denote the resins which are prepared by reacting dihydric phenols with phosgene or carbonate diesters of the dihydric phenols. Preferably, the polycarbonate resins comprise bisphenols and more preferably 2,2-bis (4'-hyroxyphenyl)propane (hereinafter, bisphenol A), a part or the whole of which may be substituted with other dihydric phenols. Examples of dihydric phenols other than bisphenol A include hydroquinone, 4,4-dihydroxydiphenyl, bis(4-hydroxyphenyl)sulfide, bis(4-hydroxyphenyl)sulfone, bis(4-hydroxyphenyl)ketone and the like. The polycarbonate resin of the present invention may be a homopolymer comprising one of the said dihydric phenols, a copolymer of two or more of the said dihydric phenols or a blend of the said homopolymer and/or copolymer.

Preferred polycarbonate resins are substantially chlorine-free polycarbonate resins that are prepared by means of an ester interchange of dihydric phenols (aromatic dihydroxy compounds) and carbonate diesters.

As used herein, the term "rubber reinforced resins" refers to all the rubber reinforce resins that comprise rubbery polymers and one or more of vinyl compounds as constituents.

Rubbery polymers having a glass transition temperature of 0 degree C. or lower are usable as constituents of the rubber reinforced resins. Examples of the rubbery polymers usable according to this invention include diene rubbers such as polybutadiene, styrene-butadiene copolymer, acrylonitrile-butadiene copolymer and the like, acrylic rubbers such as butyl polyacrylate and the like, polyisoprene, polychloroprene, ethylene-propylene copolymers, ethylene-propylene-diene ter-polymers, and block copolymers such as styrene-butadiene block copolymers, styrene-isoprene block copolymers and the like and hydrogenated compounds obtained therefrom. Of them, polybutadiene, styrene-butadiene copolymers, acrylonitrile-butadiene copolymers, butyl polyacrylate and the like are preferred.

1–95 percent by weight, preferably 5–45 percent by weight and more preferably 10–40 percent by weight of the rubbery polymer is used based on the total weight of the rubber reinforced resin and its ratio may be determined according to the mechanical strength, rigidity and moldability required.

Examples of the vinyl compounds which are constituents of the rubber reinforced resins include aromatic vinyl compounds such as styrene, α-methylstyrene, p-methylstyrene and the like, alkyl acrylates/methacrylates such as methyl methacrylate, methyl acrylate, butyl acrylate, ethyl acrylate and the like, acrylic/methacrylic acids such as acrylic acid, methacrylic acid and the like, vinyl cyanide monomers such as acrylonitrile, methacrylonitrile and the like, α, β-unsaturated carboxylic acids such as maleic anhydride and the like, maleimide monomers such as N-phenylmaleimide, N-methylmaleimide, N-cyclohexylmaleimide and the like, and glycidyl group containing monomers such as glycidyl methacrylate and the like. Preferred are aromatic vinyl compounds, alkyl acrylates/methacrylates, vinyl cyanide monomers and maleimide monomers, and more preferred are styrene, acrylonitrile, N-phenylmaleimide and butyl acrylate. These vinyl compounds may be used individually or in combinations of two or more of them. Preferable is a combination of an aromatic vinyl compound and a nonaromatic vinyl compound. In this case, the ratio of the aromatic compound to the nonaromatic compound is variable but the preferable amount of the nonaromatic compound ranges from 5 to 80 percent by weight based on the total weight of the vinyl compounds.

The rubber reinforced resins, for which the production method is not limited to a specific one, may be obtained, for example, by graft polymerizing one or more of the vinyl compounds in the presence of a rubbery polymer or by mixing a copolymer separately prepared from one or more of the vinyl compounds with the copolymer obtained as a result of the said graft polymerization. Examples of thus obtained resins are acrylonitrile-butadiene-styrene resins (ABS resins), acrylonitrile-butyl acrylate-styrene resins (AAS resins), high impact polystyrene resins (HIPS) and the like.

In case of using a blend of the polycarbonate resin and the rubber reinforced resin, the ratio of the polycarbonate resin to the rubber reinforced resin is 1–99 percent by weight to 99–1 percent polycarbonate by weight. The ratio may be determined within the above ratio range according to the mechanical strength, rigidity, moldability, and heat resistance required. The ratio of the polycarbonate resin to the rubber reinforced resin is preferably 20–95 percent polycarbonate by weight to 80–5 percent rubber reinforced resin by weight, more preferably 30–90 percent polycarbonate by weight to 70–10 percent rubber reinforced resin by weight.

Polyphenylene ether resins denote homopolymers or copolymers having the repeating unit represented by the following general formula (2) and/or (3):

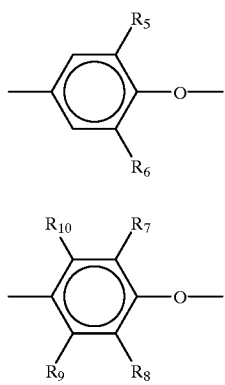

wherein $R_5$, $R_6$, $R_7$, $R_8$, $R_9$ and $R_{10}$ independently represent an alkyl group having 1 to 4 carbon atoms, an aryl group, a halogen atom or a hydrogen atom, provided that $R_9$ and $R_{10}$ are not both hydrogen atoms.

Representative examples of the polyphenylene ether homopolymer resins include poly(2,6-dimethyl-1,4-phenylene)ether, poly(2-methyl-6-ethyl-1,4-phenylene ether, poly(2,6-diethyl-1,4 -phenylene)ether, poly(2-ethyl-6-n-propyl-1,4-phenylene)ether, poly(2,6-di-n-propyl-1,4-phenylene)ether, poly(2-methyl-6-n-butyl-1,4-phenylene) ether, poly(2-ethyl-6-isopropyl-1,4-phenylene)ether, poly (2-methyl-6-hydroxyethyl-1,4-phenylene) ether, poly(2-methyl-6-chloroethyl-1,4-phenylene)ether and the like. Of these, poly(2,6-dimethyl-1,4-phenylene)ether is particularly preferable.

The polyphenylene ether copolymers are copolymers which have a structure comprising phenylene ethers as major monomer units. Examples of them include copolymers of 2,6-dimethyl phenol and 2,3,6-trimethyl phenol, copolymers of 2,6-dimethyl phenol and o-cresol and copolymers of 2,6-dimethyl phenol, 2,3,6-trimethyl phenol and o-cresol, and the like.

The polyphenylene ether resins according to this invention may contain other phenylene ether unit structures which have been proposed to be constituents of conventional polyphenylene ether resins. Examples of these units, which are proposed to be able to coexist together in small quantities, are 2-(dialkyl aminomethyl)-6-methyl phenylene ether units, 2-(N-alkyl-N-phenyl aminomethyl)-6-methyl phenyl ether units and the like described in Japanese Patent Application No. 63-12698 and JP-A-63-301222.

The polyphenylene ether resins include a polyphenylene ether resin which contains a small quantity of diphenoquinone units in its main chain.

The polyphenylene ether resins further include a polyphenylene ether modified by a C—C double bond containing compound, for example, as described in JP-A-2-276823, JP-A-63-108059 and JP-A-59-59724.

The polyphenylene ether resins of the present invention, of which the production method is not especially restricted, may be prepared by the oxidative coupling polymerization of 2,6-xylenol in the presence of dibutylamine according to a production method, for example, as described in U.S. Pat. No. 4,788,277, corresponding to Japanese Patent Application No. 62-77570. According to the present invention the molecular weight and molecular weight distribution of the polyphenylene ether resins are not restricted to specific values.

Polystyrene resins may be blended with the polyphenylene ether resins at various ratios. Preferably the ratio of the polystyrene resins to the polyphenylene ether resins is 90–1 percent polystyrene by weight to 10–99 percent polyphenylene ether by weight.

The polystyrene resins according to the present invention denote vinyl aromatic polymers and rubber modified vinyl aromatic polymers.

Examples of the vinyl aromatic polymers include polymers of styrene, alkyl ring-substituted styrene such as o-methyl styrene, p-methyl styrene, m-methyl styrene, 2,4-dimethyl styrene, ethyl styrene, p-tert-butyl styrene and the like, α-alkyl substituted styrenes such as α-methyl styrene, α-methyl-p-methyl styrene and the like, copolymers of one or more of them and at least one of the other vinyl compounds and copolymers of two or more of them. Examples of compounds copolymerizable with the said vinyl aromatic compounds are methacrylate esters such as methyl methacrylate, ethyl mathacrylate and the like, unsaturated nitrile compounds such as acrylonitrile, methacrylonitrile and the like and acid anhydrides such as maleic anhydride and the like. Of the vinyl aromatic polymers, polystyrene and styrene-acrylonitrile copolymers (AS resins) are particularly preferable.

Rubbers to be used for the rubber modified vinyl aromatic polymers include polybutadiene, styrene-butadiene copolymer, polyisoprene, butadiene-isoprene copolymer, natural rubber and ethylene-propylene copolymer. Of these, polybutadiene and styrene-butadiene copolymer are especially preferable. HIPS and ABS resins are preferable as rubber modified aromatic polymers.

Component (B) of the present invention denotes organic phosphorus compounds represented by formula (1). In the formula, n is a positive integer and ranges preferably from 1 to 10. Furthermore, at least one of the substituents indicated by $R_1$, $R_2$, $R_3$ and $R_4$ is a phenyl group, at least one of them is a xylyl group and the others are phenyl groups or xylyl groups. Preferably, compounds in which the ratio of phenyl groups to xylyl groups ranges from 1:1 to 1:3 are used because the resin composition containing them has an excellent balance of flowability and heat resistance. Of the xylyl groups, the 2,6-xylyl group is especially excellent from the viewpoint of the heat resistance and hydrolytic resistance of the resultant resin composition. If $R_1$, $R_2$, $R_3$ and $R_4$ are all phenyl groups or if they are all tolyl groups, the resultant resin composition degrades in heat resistance and flame retardance. If $R_1$, $R_2$, $R_3$ and $R_4$ are all xylyl groups, economical disadvantages are brought about due to slow reaction rate; furthermore handling becomes difficult due to elevated viscosity and the resultant resin composition deteriorates in flowability and mechanical properties Component (B) is usually a mixture of the compounds represented by formula (1) in which the ratio of phenyl groups to xylyl groups varies and the value of n also varies.

When component (B) is a mixture which consists of the compounds having various n values, the weight-average value of n ranges from 1 to 5 in general. It has been found that a smaller weight-average value of n for compounent (B) imparts a higher resin compatibility and flame retarding effect to the resin composition. The resin composition which contains the compound with n=1 is especially excellent and balanced in flowability and heat retardance and moreover, it astonishingly shows a flame-retarding effect exceeding that of triaryl phosphate esters. Accordingly, it is preferable that component (B) is a mixture comprising 50 percent by weight or more of the compound with n=1 and having a weight-average value of n in the range of from 1 to 3. It is especially preferable that the component is a mixture containing 60 percent by weight or more of the compound with n=1 and having a weight-average value of n in the range of from 1 to 2.

The content of component (B) varies according to the kind of component (A) used and the desirable flame retardance grade of the resultant resin composition, and from 0.1 to 30 parts by weight of component (B) is necessary based upon 100 parts by weight of component (A). The satisfactory flame retardance of the resultant resin composition is not obtained if the content of component (B) is less than 0.1 part by weight. If the content of component (B) is more than 30 parts by weight, the resultant resin composition deteriorates in mechanical properties. The content component (B) ranges preferably from 0.5 to 20 parts by weight, more preferably from 5 to 20 parts by weight.

According to the present invention, the compounds of component (B) which have desirable structures may be prepared effectively and selectively by means of a three-stage process consisting of reacting an oxyhalogenated phosphorus with bisphenol A, further reacting xylenol with the resultant product and adding phenol thereto to complete the series of the reaction stages.

In the first reaction stage, bisphenol A is reacted with an oxyhalogenated phosphorus in the presence of a Lewis acid catalyst or the like to obtain a composition mainly comprising phosphoric dimers. The unreacted oxyhalogenated phosphorus is removed from the composition by means of distillation or the like by necessity in order to prevent the production of by-products, triaryl phosphate esters such as triphenyl phosphate and the like. In the second reaction stage, xylenol is reacted with the resultant product of the first reaction stage at a ratio of 1–3 moles per mole of the bisphenol A used in the first reaction stage, the ratio varying according to the desired compositions of the products. In the third reaction stage, phenol is added at the ratio of more than the equivalent weight of the unreacted halogen bonded with phosphorus to complete a series of the reaction stages. Unreacted phenol is removed by means of distillation or the like by necessity and the desired compounds are obtained after removing the catalyst and residual halogens by means of washing and/or filtering or the like.

The production method for the organic phosphorus compounds according to the present invention utilizes the principle that the rate of xylenol reaction with the resultant product of the first reaction stage decreases as the substituted xylyl groups increase in number because of the bulky nature of the xylenol, i.e., its steric hindrance effects. Accordingly, 2,6-xylenol, having higher steric hindrance effects than any other xylenol, is preferable to obtain desirable organic phosphorus compounds.

Of oxyhalogenated phosphorus compounds, phosphorus oxychloride is preferable from the viewpoint of reactivity and easy handling.

Referring now to the ratio of the feed material in the first reaction stage, 1.5–10 moles, preferably 1.7–8 moles, more preferably 1.8–5 moles of an oxyhalogenated phosphorus is used per mole of bisphenol A. Accordingly, as the mole ratio of the oxyhalogenated phosphorus decreases, the weight-average value of n in formula (1) becomes larger. If the oxyhalogenated phosphorus is supplied at the ratio of 1.5 mole or less per mole of the bisphenol A, the reactant gels. If oxychlorinated phosphorus is supplied at the ratio of 2 moles or more per mole of the bisphenol A, it will be preferable to remove the unreacted oxyhalogenated phosphorus by means of distillation or the like after the first reaction stage is completed, in order to prevent the production of the by-product, i.e., the triaryl phosphate ester in the second reaction stage and thereafter.

In the production method for the organic phosphorus compounds of the present invention, the composition of the product may be controlled by varying the amount of the xylenol added in the second reaction stage. Namely, it is possible to obtain the product whose molecules may contain xylyl groups in the ratio variable at will from small to large by supplying xylenol at the ratio of 1–3 moles xylenol per mole of bisphenol A. The ratio of 1.0–2.0 moles is particularly preferable for obtaining the product that is suitable for a flame retardant. If it is lower than the lowest limit, the flame retardance, heat resistance and other properties of the resultant resin composition deteriorate due to the production of moieties containing no xylyl group, while if the ratio exceeds 3 moles, the viscosity of the reactant increases greatly and the reaction rate lowers extremely due to the production of moieties containing no phenyl group. Furthermore, bleeding tends to occur because the flowability of the resultant resin composition deteriorates and because its hydrolytic action heightens. On the other hand, it is important to control reaction temperature so as to selectively obtain the organic phosphorus compounds having the desirable ratio of xylyl groups. The reaction temperature ranges from 50 to 200 degrees C., preferably from 60 to 180 degrees C., more preferably from 70 to 160 degrees C. At the reaction temperature of lower than 50 degrees C., satisfactory reaction rate is not obtained, while at the reaction temperature of more than 200 degrees C. the production ratio of the moieties containing neither xylyl nor phenyl group increases because the selective reactivity of xylenol becomes low.

In the third reaction stage, the quantity of phenol to be supplied should equal or exceed that of the unreacted halogen atoms bonded with phosphorus atoms at the end of the second reaction stage.

Furthermore, in the third reaction stage, the ester interchange reaction of phenol groups and the disproportionation reaction, for example, one molecule of a triaryl phosphate ester and one molecule of the compound (with n=2) represented by formula (1) being each produced from two molecules of the compound (with n=1) represented by formula (1), take place in a parallel way. The above side reactions tend to occur more frequently as the reaction temperature rises. Accordingly, it is necessary to keep the reaction temperature at 200 degrees C. or lower even in the third reaction stage. The reaction is to be completed at the reaction temperature of preferably 180 degrees C. or lower, more preferably 160 degrees C. or lower. The lowest limit is not placed particularly upon the reaction temperature, but 60 degrees C. or higher is usually preferable in consideration of the reaction rate.

On the other hand, the reaction rate of the third reaction stage is low due to the steric hindrance of substituents of the reaction products in the second reaction stage. Accordingly, besides the addition of the lewis acid catalyst in the first reaction stage it is preferable to add a catalyst in the second and/or the third reaction stage in which the reaction rate is low.

Examples of Lewis acid catalysts include aluminum chloride, titanium tetrachloride, iron chloride, magnesium chloride, tin chloride, zinc chloride, antimony pentachloride and the like. In the first reaction stage, the preferable catalyst is anhydrous magnesium chloride which has a high reaction selectivity and which does not bring about gelation. In the second and/or the third reaction stage, the preferable catalyst to be additionally fed is anhydrous aluminum chloride which is highly active as a catalyst.

If the quantity of catalyst is too low, the reaction rate is lowered, whereas if the catalyst amount is excessive, ester interchange reactions and disproportionation are promoted.

In the first reaction stage, the amount of catalyst to be added ranges from $10^{-3}$ to $10^{-1}$ mole, preferably from $5 \times 10^{-3}$ to $5 \times 10^{-2}$ mole per mole of the bisphenol A. In the second and/or the third reaction stage, the amount of the catalyst to be added ranges from $10^{-3}$ to $10^{-1}$ mole per mole of the bisphenol A to be supplied in the first reaction stage. In the first through the third reaction stages, the total amount of the catalyst to be supplied ranges $10^{-3}$ to $2 \times 10^{-1}$ mole per mole of the bisphenol A to be supplied in the first reaction stage.

After the third reaction stage, unreacted phenol is removed from the reaction product by means of distillation or the like according to necessity. Even in this stage, side reactions such as ester interchange and disproportionation take place at high temperatures. It is, therefore, necessary to keep the operation temperature at 200 degrees C. or lower, preferably at 180 degrees C. or lower, more preferably at 160 degrees C. or lower. The lowest limit is not placed particularly upon the reaction temperature, but 140 degrees C. or higher is preferable as the lowest limit in consideration of maintaining a practical distillation rate.

In a refining process for the crude organic phosphorus compounds obtained, the residual halogens are removed and the Lewis acid catalysts are removed or inactivated. The refining process is not especially restricted, but a preferable process comprises adding pure water, alkaline water, acidic water or the like to the crude organic phosphorus compounds, agitating and washing to decompose the Lewis acid catalysts and to leach out the metals and the residual halogens of the decomposed catalysts therefrom to an aqueous phase, and further separating the organic phosphorus compounds from the aqueous phase and drying them. The Lewis acid catalyst-free organic phosphorus compounds thus obtained are thermally stable and hardly volatilize, decompose and/or denature even at 300 degrees C.

The process for producing the organic phosphorus compounds of this invention may be carried out in the presence or absence of a solvent such as xylene or the like. A portion of the organic phosphorus compounds produced during the process may be preferably employed as a solvent.

Even if a dihydric phenol, a phenol having two alkyl groups at the 2 and 6 positions and a phenol having no substituent at the 6 position are used instead of bisphenol A, xylenol and phenol, a corresponding organic phosphorus compound may be obtained at a high selectivity according to the aforesaid organic phosphorus compound production process.

There are other processes for preparing organic phosphorus compounds than those described hereinbefore. For example, JP-B-62-25706 describes a process which comprises supplying an oxyhalogenated phosphorus, a monohydric phenol and a dihydric phenol at the same time and carrying out their reaction, and JP-B-54-32818 and JP-A-5-1079 describe a process in which, after a monohydric phenol is reacted with an oxyhalogenated phosphorus, the reaction is completed by adding a dihydric phenol. These processes have the drawback of producing a great quantity of by-products such as triaryl phosphate esters and compounds whose substituents are all either phenyl groups or xylyl groups. JP-A-63-227632 describes a process in which a dihydric phenol is reacted with an oxyhalogenated phosphorus and then a monohydric phenol is added to complete the reaction, but this process is unsatisfactory in that the compound whose substituents are all phenyl groups tends to be produced because the phenol, having a high reactivity, reacts selectively and it is difficult to complete the reaction of xylenol. Moreover, in any of the above-mentioned processes, the yield of desirable compounds will lower because side reactions such as the foregoing ester interchange, disproportionation and the like take place if the reaction temperature is elevated to 200 degrees C. or higher.

Besides component (B), the resin composition of the present invention may contain, in such quantities as allowable according to the present invention, other organic phosphorus compounds [hereinafter, component (C)] such as compounds of formula (1) wherein $R_1$, $R_2$, $R_3$ and $R_4$ are all phenyl groups or xylyl groups, triaryl phosphate esters and the like. Usually, the amount of any one compound present in component (C) is no more than 30 percent by weight of the total amount of component (C), and the amount of all component (C) materials is no more than 40 percent by weight of the total quantity of all (B) and (C) components. If one of the above values is exceeded each value of the above with regard to component (C), it is difficult for the resin composition of this invention to retain its good balance of flame retardance, heat resistance, flowability and blooming resistance.

It is effective and preferable to use dripping inhibitors together with component (B). Examples of the dripping inhibitors include perfluoroalkane polymers such as polytetrafluoroethylene, silicone rubbers, acryl-silicone composite rubbers and the like.

Of the above, particularly preferable is polytetrafluoroethylene, whose amount ranges preferably from 0.01 to 3 parts by weight, more preferably from 0.05 to 2 parts by weight, based on 100 parts by weight of component (A). In case of less than 0.01 parts by weight drippping inhibitor, the effectiveness of the dripping inhibitor is unsatisfactory during burning and high flame retardance cannot be obtained, while in case of more than 3 parts by weight, moldability and rigidity deteriorate with regard to the resultant resin composition.

The acryl-silicone composite rubber denotes a graft copolymer obtained by graft polymerizing one or more of vinyl compounds with a composite rubber consisting of 10–90 percent by weight of an organopolysiloxane rubber constituent and 90–10 percent by weight of a polyalkyl acrylate/methacrylate rubber constituent, totaling 100 percent by weight and having a structure of the two being interwined with each other.

The vinyl compounds include aromatic vinyl compounds such as styrene, α-methylstyrene, p-methylstyrene and the like, alkyl acrylates/methacrylates such as methyl methacrylate, methyl acrylate, butyl acrylate, ethyl acrylate and the like, acrylic/methacrylic acids such as acrylic acid, methacrylic acid and the like, vinyl cyanide monomers such as acrylonitrile, methacrylonitrile and the like, α,β-unsaturated carboxylic acids such as maleic anhydride and the like, maleimide monomers such as N-phenyl maleimide, N-methyl maleimide, N-cyclohexyl maleimide and the like, and glycidyl group containing monomers such as glycidyl methacrylate and the like. Of these, preferable are aromatic vinyl compounds, alkyl acrylates/methacrylates, vinyl cyanide monomers and maleimide monomers, and more preferable are styrene, acrylonitrile, N-phenyl maleimide, butyl acrylate and methyl methacrylate. These vinyl compounds may be used individually or in a combination of two or more. The organopolysiloxane rubber and the polyalkyl acrylate/methacrylate rubber, which are constituents of the composite rubber, cannot be separated from each other from a structural viewpoint. Preferably, the particle size of the composite rubber ranges from 0.08 to 0.6 μm. The composite rubber having such a structure may be manufactured, for example, by the techniques described in JP-A-64-79257 and JP-A-1-190746.

The content of the acryl-silicone composite rubber ranges preferably from 0.01 to 10 parts by weight, more preferably from 0.05 to 5 parts by weight, based on 100 parts by weight of component (A). In the case of less than 0.01 parts by weight, dripping inhibition effects are insufficient and satisfactory flame retardance cannot be obtained, while in case of more than 10 parts by weight, moldability and rigidity of the resultant resin composition deteriorate.

Inorganic fillers such as glass fibers, glass flakes, glass beads, calcium carbonate, talc, mica and the like and reinforcing materials such as carbon fibers, charcoal and the like may be added to the resin composition of the present invention in order to improve its properties. Their amount ranges preferably from 0.01 to 60 parts by weight, more preferably from 5 to 55 parts by weight, based upon 100 parts by weight of component (A).

Furthermore, conventional additives such as lubricants, antistatic agents, antioxidants, ultraviolet light absorbers, colorants, titanium oxides, surface modifiers, dispersants, plasticizers, stabilizers and the like may be added.

The resin composition of the present invention, of which production method is not limited to a specific one, may be prepared by a conventional method, for example, melt kneading by extrusion.

BEST MODE FOR CARRYING OUT THE INVENTION

Various embodiments of this invention are further described and illustrated by the following examples.

The following are methods for analyzing organic phosphorus compounds.

1. Quantitative Analysis of Products
   (1) Determination of n value:
   Equipment: GPC (Tosoh Corp.)
   Column: TSKgel G2000HXL 2 Units (Tosoh Corp.)
   TSKgel G3000HXL 1 Unit (Tosoh Corp.)
   The columns are connected in series
   Solvent: THF, Flow rate: 1 ml/min.
   Detector: UV, $\lambda$=254 nm
   Sample: diluted 200 times by volume with THF
   Volume added: $5\mu$ liters
   Quantitative determination: absolute calibration curve method
   (2). Analysis of dimer(n=1 constituent):
   Equipment: LC-10A (Shimazu Corp.)
   Column: TSKgel ODS-80T (Tosoh Corp.)
   Solvent: Methanol/water=90/10 by weight,
      Flow rate: 0.5 ml/min.
   Detector: UV, $\lambda$=254 nm
   Sample: diluted 100 times by volume with methanol
   Volume added: $10\mu$ liters
   Quantitative determination method: area ratio
2. Analysis of Constituents
   Equipment: LC-MS (Model: Hitachi API)
   Column: TSKgel ODS-80T (Tosoh Corp.)
   Solvent: Methanol/water=95/5 by weight,
      Flow rate: 1 ml/min.
   Sample: diluted 100 times by volume with methanol
   Volume added: $10\mu$ liters
   Ionization: Drift voltage: 180v
      Atomized chamber: 280° C.
      Desolvating chamber: 350° C.
   Determination range: m/e 200–1000

The following are materials were used for examples and comparative examples.

1. Resins
   Polycarbonate resin A-1
      Polycarbonate resin having a weight-average molecular weight of 24,500
   Rubber reinforced resin A-2
      ABS resin which comprises 29.7 wt. % of butadiene units, 19.0 wt. % of acrylonitrile units and 51.3 wt. % of styrene units
   Rubber reinforced resin A-3
      AAS resin which comprises 20 wt. % of butyl acrylate rubber constituent, 24 wt. % of acrylonitrile units and 56 wt. % of styrene units
   Rubber reinforced resin A-4
      HIPS resin which comprises 12 wt. % of butadiene rubber constituent and 88 wt. % of styrene units
2. Organic phosphorus compounds
   Organic phosphorus compound B-1
      The organic phosphorus compound represented by formula (4) wherein the ratio of xylyl groups to phenyl groups is 1:2.5 and the weight-average value of n is 1.5

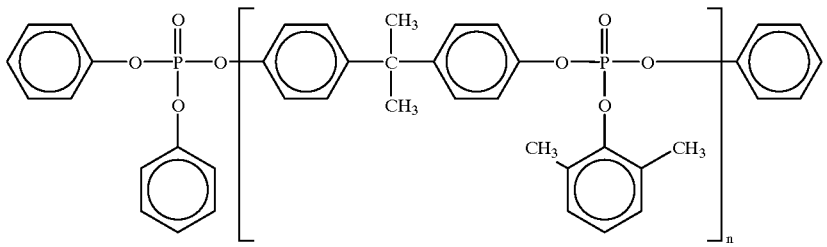

(4)

Organic phosphorus compound B-2
      The organic phosphorus compound represented by formula (4) wherein the ratio of xylyl groups to phenyl groups is 1:2.3 and the weight-average value of n is 2.5
   Organic phosphorus compound B-3
      Triphenyl phosphate (TPP) represented formula (5)

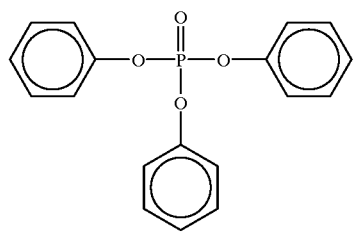

(5)

Organic phosphorus compound B-4
      Bisphenol A polycresylphosphate represented by formula (6) wherein the weight-average value of n is 1.6

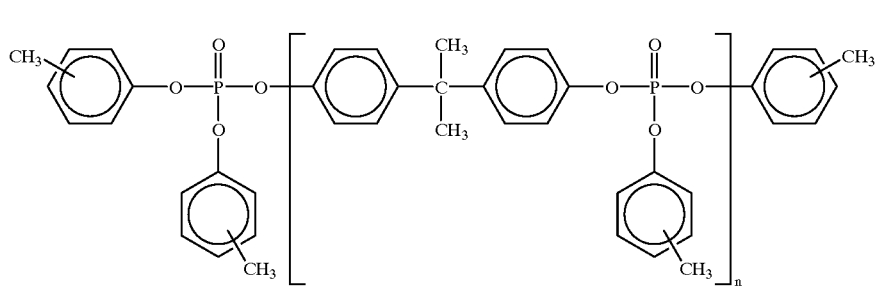

(6)

Organic phosphorus compound B-5
  A mixture consisting of 96 wt. % of organic phosphorus compounds represented by formula (4) wherein the ratio of xylyl groups to phenyl groups is 1:2.5 and the weight-average value of n is 1.3, 2 wt. % of triphenylphosphate represented by formula (5) and 2 wt. % of the organic phosphorus compound represented by formula (7)

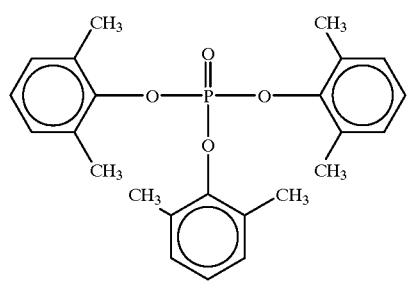

(7)

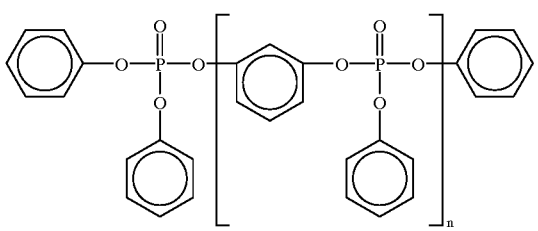

(9)

Organic phosphorus compound B-6
  A mixture consisting of 95 wt. % of the organic phosphorus compound represented by formula (8) wherein the weight-average value of n is 1.5 and 5 wt. % of triphenylphosphate represented by formula (5)

3. Other additives
  Additive C-1
    Acryl-silicone composite rubber: a graft copolymer consisting of 100 parts by weight of organopolysiloxane latex, 37.5 parts by weight of n-butyl acrylate, 2.5 parts by weight of allyl methacrylate and 30 parts by weight of methyl methacrylate (Graft copolymer obtained according to the method described in Reference 1 and the Examples of JP-A-64-79257 wherein methyl methacrylate is used instead of a liquid mixture of acrylonitrile and styrene for graft polymerization)
  Additive: C-2
    Polytetrafluoroethylene having an average particle size of 500 μm

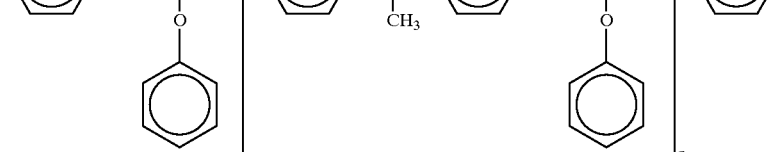

(8)

Organic phosphorus compound B-7
  The organic phosphorus compounds represented by formula (8) wherein the weight-average value of n is 1.3
Organic phosphorus compound B-8
  The organic phosphorus compounds represented by formula (9) wherein the weight-average value of n is 1.5

EXAMPLES 1–5 AND COMPARATIVE EXAMPLES 1 AND 2

The resins prepared as described hereinbefore were blended according to the compositions shown in Table 1 on a part-by-weight basis to obtain resin compositions. The compositions were each melt kneaded and pelletized with a twin screw extruder in which the barrel temperature was set at 240 degrees C., and were further molded into test pieces for property evaluation, combustion testing and blooming evaluation with an injection molding machine in which cylinder temperature was 250 degrees C. and in which mold temperature was 65 degrees C. Table 2 shows the results obtained for the test pieces according to the following evaluation methods.

Flame retardance: Evaluated according to the horizontal flame test as described in UL-94, using test pieces of 1/12 inch thickness.

Izod impact strength: Evaluated according to ASTM D256 using notched test pieces of 1/8 inch thickness, expressed in kg-cm/cm.

Melt flow rate (MFR): Determined by JIS K7210, at 220 degrees C. under load of 10 kg, expressed in g/10 min.

Heat distortion temperature (HDT): Determined by ASTM D648, using test pieces of 1/8 inch thickness under a load of 18.6 kg/cm$^2$, expressed in degrees Centigrade.

Blooming: Test piece immersed in water of 80 degrees C. for 150 hours, followed by visual observation of one side and classification as follows:

o: No blooming of phosphate esters, strength retained

X: Blooming of phosphate esters observed, strength deteriorated

EXAMPLES 6–10 AND COMPARATIVE EXAMPLES 3 AND 4

Evaluation was carried out in the same way as in Example 1 except for the following evaluation method. Each composition was as shown in Table 3 and evaluation results are shown in Table 4.

Flame retardance: Evaluated according to the horizontal flame test as described in UL-94, using test pieces of 1/8 inch thickness.

EXAMPLES 11–15 AND COMPARATIVE EXAMPLES 5 AND 6

Evaluation was carried out in the same manner as in Example 1 except for the following evaluation methods. Each composition was as shown in Table 5 and evaluation results are shown in Table 6.

Izod impact strength: Evaluated according to ASTM D256, using notched test pieces of 1/4 inch thickness, expressed in kg-cm/cm.

Heat distortion temperature (HDT): Determined by ASTM D648, using test pieces of 1/8 inch thickness and under a load of 18.6 kg/cm$^2$, expressed in degrees Centigrade.

Blooming: measured in terms of the weight loss of pelletized resin samples with a thermobalance (Seiko TG/DATA 220) after heating at a rate of 20° C./min. in a nitrogen gas atmosphere. Because weight loss quantities reflected the volume of gas generated (blooming quantity) at the time of molding, the comparative evaluation of the pelletized resin samples was made by the weight loss quantities (numerically by wt. %) at 280 degrees C. The smaller the numerical value, the less the volume of gas generated and the less the blooming.

EXAMPLES 16–18 AND COMPARATIVE EXAMPLES 7–10

Resin compositions were evaluated in accordance with the following methods and conditions.

Flame retardance: Determined by the horizontal flame test as described in UL-94, using test pieces of 1/8 inch thickness.

Smoke emission: Determined by visually observing the quantity of smoke emitted from the nozzle of an injection molding machine during purging of the resin compositions.

Stability of resin compositions: The changes of water content and dielectric loss tangent in a hydrolysis promotion test were employed as indices for water absorption and electrical properties of the test pieces to evaluate the stability of the resin compositions. The hydrolysis promotion test was carried out by putting the test pieces under saturated water vapor of 2 atms. at 120 degrees C. for 200 hours. In the test, the water absorption was measured by determining the difference of the test piece weight before and after promoting hydrolysis. The dielectric loss tangent was determined at 23 degrees C. and 60 Hz according to ASTM D150.

Heat distortion temperature (HDT): Determined by ASTM D648, using test pieces of 1/4 inch thickness and under a load of 18.6 kg/cm$^2$, as expressed in degree Centigrade.

Melt flow rate (MFR): Determined by JIS K7210 at 250 degrees C. under a load of 10 kg, expressed in g/10 min.

Example 16

14 parts by weight of organic phosphorus compound B-1, 1.0 part by weight of zinc oxide and 0.3 part by weight of octadecyl-3-(3-5-di-t-butyl-4-hydroxyphenyl)propionate were mixed with 100 parts by weight of the resin composition consisting of 67 parts by weight of poly-2,6-dimethyl-1,4-phenylene ether (hereinafter, PPE) having the intrinsic viscosity ($\eta$) of 0.47 in chloroform at 30 degrees C., 24 parts by weight of a high impact polystyrene resin (hereinafter called HIPS, Asahi Kasei Polystyrene 492, a product of Asahi Kasei Kogyo K.K.) and 9 parts by weight of a polystyrene resin (hereinafter called GPPS, Asahi Kasei Polystyrene 685, a product of Asahi Kasei Kogyo K.K.) to obtain a mixture. It was melt kneaded with a twin screw extruder with the barrel temperature was set at 300 degrees C. to obtain pellets. The pellets were injection molded and evaluated. The evaluation results are shown in Table 7.

Example 17

Example 16 was repeated except that 11 parts by weight of organic phosphorus compound B-1 was used instead of 14 parts by weight of said compound. Evaluation was carried out in the same way as in Example 16 and the results are shown in Table 7.

Comparative Examples 7–9

Respective components were mixed as shown in Table 7. Evaluation was carried out as in Example 17 and the evaluation results are also shown in Table 7.

Example 18

100 parts by weight of PPE and 18 parts by weight of organic phosphorus compound B-1 were melt kneaded with a twin screw extruder with the barrel temperature set at 320 degrees C. to obtain pellets. The pellets were injection molded and evaluated. The evaluation results are shown in Table 8.

Comparative Example 10

Example 18 was repeated except that organic phosphorus compound B-8 was used instead of organic phosphorus compound B-1. Evaluation was carried out in the same way as in Example 18 and the results are shown in Table 8.

EXAMPLE 19 AND COMPARATIVE EXAMPLES 11–13

The resin compositions were prepared by blending according to the compositions shown in Table 9 on a part-by-weight basis and melt kneaded and pelletized with a twin screw extruder with the barrel temperature set at 240 degrees C. and molded into test pieces for property evaluation and burning tests by the use of an injection molding machine with a cylinder temperature of 250 degrees C. and a mold temperature of 65 degrees C. The test pieces were evaluated and the results are shown in Table 10.

Flame retardance: Evaluated according to the horizontal flame test as described in UL-94, using test pieces of 1/12 inch thickness and 1/16 inch thickness.

Izod impact strength: Determined by ASTM D256, using notched test pieces of 1/4 inch thickness, expressed in kg-cm/cm.

Heat distortion temperature (HDT): Determined by ASTM D648, using test pieces of 1/8 inch thickness and under a load of 18.6 kg/cm$^2$, expressed in degrees Centigrade.

EXAMPLE 20

114 grams (0.5 mol) of bisphenol A, 154 g (1.0 mol) of phosphorus oxychloride and 1.4 g (0.015 mol) of anhydrous magnesium chloride were supplied to a 500 ml four-necked flask equipped with an agitator and a reflux tube and reacted under a nitrogen flow at a temperature of 70–140 degrees C. for 4 hours in the 1st reaction stage.

After the reaction was completed, the pressure within the flask was reduced to 200 mmHg or lower with a vacuum pump while the reaction temperature was being maintained and unreacted phosphorus oxychloride was recovered with a trap.

The flask was cooled to room temperature. Then 61 g (0.5 mol) of 2,6-xylenol and 2.0 g (0.015 mol) of anhydrous aluminum chloride were added and reacted for four hours at a temperature of 100–150 degrees C. in the 2nd reaction stage.

Subsequently, the flask was cooled to room temperature. Then 141 g (1.5 mol) of phenol was added. The flask was then heated to a temperature of 100–150 degrees C., which was maintained for four hours to complete the reaction in the 3rd reaction stage.

As the flask temperature was being maintained, the flask pressure was reduced to 2 mmHg to distill off unreacted phenol.

Hydrogen chloride gas generated during the reaction was collected by an aqueous sodium hydroxide solution and the quantity evolved was determined by means of a neutralization titration to monitor the progress of the reaction.

The reaction product was washed with an acid and distilled water and vacuum dried to obtain a light yellow, transparent composition consisting of the organic phosphorus compounds represented by formula (4) as a major component. The results obtained by analyzing the composition are shown in Table 11. The composition contained 87 percent by weight of component (B) with a weight-average value of n was 1.5.

EXAMPLE 21

Example 20 was repeated except that 192 g (1.25 mols) of phosphorus oxychloride was used in the first reaction stage, 122 g (1.0 mol) of 2,6-xylenol was used in the second reaction stage and 94 g (1.0 mol) of phenol was used in the third reaction stage to obtain a light yellow, transparent composition comprising as a major component the organic phosphorus compound represented by formula (10). The results obtained by analyzing the composition are shown in Table 11. The composition contained 96 percent by weight of component (B) with a weight-average value of n of 1.3.

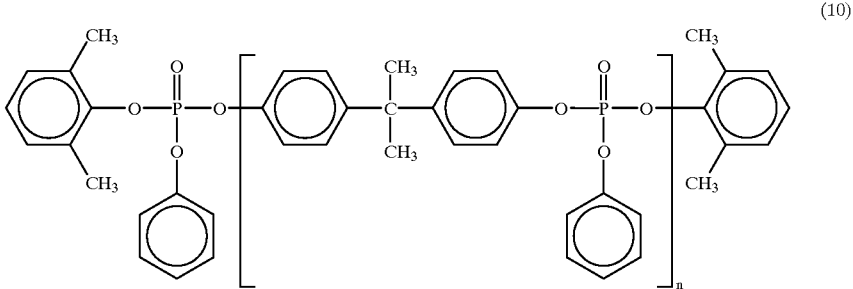

(10)

COMPARATIVE EXAMPLE 14

Example 21 was repeated except that the second reaction stage, the 3rd reaction stage and the removal of unreacted phenol by distillation were carried out at 220 degrees C. to obtain a brown, viscous product. The results obtained by analyzing the product are shown in Table 11. The product contained 48 percent by weight of component (C) with a weight-average value of n of 3.1.

EXAMPLES 22 AND 23

Example 1 was repeated except that 75 parts by weight of polycarbonate resin A-1, 25 parts by weight of rubber reinforced resin A-2, 15 parts by weight of the organic phosphorus compound obtained in either Example 20 or 21 and 0.3 parts by weight of additive C-2 were mixed and processed into test pieces. The results obtained by evaluating the test pieces according to the following methods and conditions are shown in Table 12.

Flame Retardance: Evaluated according to the horizontal flame test as described in UL-94, using test pieces of 1/16 inch thickness.

Heat distortion temperature (HDT): Determined by ASTM D648, using test pieces of 1/4 inch thickness and under a load of 18.6 kg/cm$^2$, expressed in degree Centigrade.

Industrial Applicability

As described and illustrated in the foregoing, the flame-retardant resin compositions of the present invention are excellent in heat resistance, thin-walled moldings prepared from the compositions have desirable impact strength and articles molded therefrom are free of surface blooming.

TABLE 1

| | Resin composition (parts by weight) | | | | | |
|---|---|---|---|---|---|---|
| | Polycarbonate (A) | | Phosphorus compound (B) | | Additive | |
| Example 1 | A-1 | 100 | B-1 | 15 | C-1 | 0.1 |
| Example 2 | A-1 | 100 | B-1 | 10 | C-1 | 0.1 |
| Example 3 | A-1 | 100 | B-1 | 20 | C-1 | 0.1 |
| Example 4 | A-1 | 100 | B-1 | 15 | C-2 | 0.3 |
| Example 5 | A-1 | 100 | B-2 | 15 | C-1 | 0.3 |
| Comparative example 1 | A-1 | 100 | B-3 | 15 | C-1 | 0.1 |
| Comparative example 2 | A-1 | 100 | B-4 | 15 | C-1 | 0.1 |

TABLE 2

| | Melt flow rate | Izod impact strength | Heat distortion temperature | Blooming | UL 94 |
|---|---|---|---|---|---|
| Example 1 | 20 | 10 | 96 | O | V-0 |
| Example 2 | 15 | 20 | 100 | O | V-0 |
| Example 3 | 26 | 8 | 93 | O | V-0 |
| Example 4 | 18 | 12 | 96 | O | V-0 |
| Example 5 | 19 | 12 | 98 | O | V-0 |
| Comparative example 1 | 24 | 10 | 80 | x | V-0 |
| Comparative example 2 | 19 | 6 | 89 | O | V-0 |

TABLE 3

| | Resin composition (parts by weight) | | | | | | | |
|---|---|---|---|---|---|---|---|---|
| | Resin (A) | | | | | | | |
| | Poly-carbonate | | Rubber reinforced resin | | Phosphorus compound (B) | | Additive | |
| Example 6 | A-1 | 70 | A-2 | 30 | B-1 | 15 | C-1 | 0.1 |
| Example 7 | A-1 | 70 | A-3 | 30 | B-1 | 15 | C-1 | 0.1 |
| Example 8 | A-1 | 70 | A-4 | 30 | B-1 | 15 | C-1 | 0.1 |
| Example 9 | A-1 | 70 | A-2 | 30 | B-1 | 15 | C-2 | 0.1 |
| Example 10 | A-1 | 90 | A-2 | 10 | B-1 | 15 | C-1 | 0.1 |
| Comparative example 3 | A-1 | 90 | A-2 | 10 | B-3 | 15 | C-1 | 0.1 |
| Comparative example 4 | A-1 | 90 | A-2 | 10 | B-4 | 15 | C-1 | 0.1 |

TABLE 4

| | Melt flow rate | Izod impact strength | Heat distortion temperature | Blooming | UL 94 |
|---|---|---|---|---|---|
| Example 6 | 35 | 30 | 92 | O | V-0 |
| Example 7 | 40 | 25 | 93 | O | V-0 |
| Example 8 | 45 | 24 | 92 | O | V-0 |
| Example 9 | 33 | 32 | 92 | O | V-0 |
| Example 10 | 31 | 35 | 95 | O | V-0 |
| Comparative example 3 | 45 | 30 | 76 | x | V-0 |
| Comparative example 4 | 34 | 23 | 85 | O | V-0 |

TABLE 5

| | Resin composition (parts by weight) | | | | | | | |
|---|---|---|---|---|---|---|---|---|
| | Resin (A) | | | | | | | |
| | Poly-carbonate | | Rubber reinforced resin | | Phosphorus compound (B) | | Additive | |
| Example 11 | A-1 | 85 | A-2 | 15 | B-5 | 10 | C-2 | 0.3 |
| Example 12 | A-1 | 85 | A-3 | 15 | B-5 | 10 | C-2 | 0.3 |
| Example 13 | A-1 | 85 | A-4 | 15 | B-5 | 10 | C-2 | 0.3 |
| Example 14 | A-1 | 85 | A-2 | 15 | B-5 | 10 | C-1 | 0.1 |
| Example 15 | A-1 | 90 | A-2 | 10 | B-5 | 15 | C-2 | 0.3 |
| Comparative example 5 | A-1 | 85 | A-2 | 15 | B-3 | 10 | C-2 | 0.3 |
| Comparative example 6 | A-1 | 85 | A-2 | 15 | B-6 | 10 | C-2 | 0.3 |

TABLE 6

| | Melt flow rate | Izod impact strength | Heat distortion temperature | Blooming* | UL 94 |
|---|---|---|---|---|---|
| Example 11 | 12 | 15 | 112 | 0.3 | V-0 |
| Example 12 | 15 | 13 | 113 | 0.3 | V-0 |
| Example 13 | 17 | 11 | 110 | 0.3 | V-0 |
| Example 14 | 13 | 15 | 112 | 0.3 | V-0 |
| Example 15 | 10 | 16 | 115 | 0.3 | V-0 |
| Comparative example 5 | 18 | 13 | 97 | 2.2 | V-0 |
| Comparative example 6 | 13 | 13 | 104 | 0.3 | V-0 |

TABLE 7

| | Ex. 16 | Ex. 17 | Comp. ex. 7 | Comp. ex. 8 | Comp. ex. 9 |
|---|---|---|---|---|---|
| Resin composition (parts by weight) | | | | | |
| PPE A-5 | 67 | 67 | 67 | 67 | 67 |
| HIPS A-6 | 24 | 24 | 24 | 24 | 24 |
| GPPS | 9 | 9 | 9 | 9 | 9 |
| (B) Phosphoric ester B-1 | 14 | 11 | | | |
| Phosphoric ester B-7 | | | | | |
| Phosphoric ester B-8 | | | 11 | 11 | |
| Phosphoric ester B-3 | | | | | 11 |
| Evaluation | | | | | |
| Flame retardance (UL 94) | V-0 | V-0 | V-0 | V-0 | V-0 |
| Smoke emission (Visual observation) | *1 | *1 | *1 | *1 | Large vol. |
| Water absorption after promoting hydrolysis (wt. %) | *2 | 1.3 | 3.2 | 22 | 10 |
| Dielectric loss tangent before promoting hydrolysis | *2 | 0.003 | 0.004 | 0.003 | 0.003 |
| Dielectric loss tangent after promoting hydrolysis | *2 | 0.004 | 0.010 | 0.088 | 0.007 |
| HDT (°C.) | 117 | 123 | 117 | 114 | 109 |
| MFR (g/10 min.) | 7.1 | 4.7 | 4.7 | 5.0 | 7.0 |

*1: Very little
*2: Not measured

TABLE 8

|  | Ex. 18 | Comp. ex. 10 |
|---|---|---|
| Resin composition (parts by weight) | | |
| PPE A-5 | 100 | 100 |
| (B) Phosphoric ester B-1 | 18 | |
| Phosphoric ester B-8 | | 18 |
| Evaluation | | |
| Flame retardance (UL 94) | V-0 | V-0 |
| Smoke emission (Visual observation) | Very little | Very little |
| Water absorption after promoting hydrolysis (wt. %) | ≦ | 20.1 |

TABLE 9

| | Resin composition (parts by weight) | | | | | | |
|---|---|---|---|---|---|---|---|
| | Resin (A) | | | | | | |
| | Poly-carbonate | | Rubber reinforced resin | | Phosphorus compound (B) | | Additive |
| Example 19 | A-1 | 85 | A-2 | 15 | B-5 | 10 | C-2 0.3 |
| Comparative example 11 | A-1 | 85 | A-2 | 15 | B-4 | 10 | C-2 0.3 |
| Comparative example 12 | A-1 | 85 | A-2 | 15 | B-6 | 10 | C-2 0.3 |
| Comparative example 13 | A-1 | 85 | A-2 | 15 | B-8 | 10 | C-2 0.3 |

TABLE 10

| | Flame retardancy, UL average burning time (sec.) | | | Heat distortion |
|---|---|---|---|---|
| | 1/12 Inch | 1/16 Inch | Izod impact strength | temperature |
| Example 19 | 0.6 | 1.8 | 15 | 112 |
| Comparative example 11 | 3.6 | 6.3 | 12 | 105 |
| Comparative example 12 | 3.7 | 9.1 | 13 | 104 |
| Comparative example 13 | 0.6 | 3.7 | 13 | 103 |

TABLE 11

| | | | Ex. 20 | Ex. 21 | Comp. ex. 14 |
|---|---|---|---|---|---|
| Composition by GPC | Triaryl phosphate ester | | 5 | 4 | 25 |
| | Organic phos-phorus compound (wt. %) | n = 1 | 63 | 75 | 22 |
| | | n = 2 | 20 | 14 | 18 |
| | | n = 3 | 8 | 5 | 12 |
| | | n > 3 | 4 | 2 | 23 |
| Weight-average value of n | | | 1.5 | 1.3 | 3.1 |
| No. of xylyl groups per molecule of organic phosphorus compound with n = 1 (wt. %) | | 0 | 8 | 0 | 12 |
| | | 1 | 63 | 15 | 25 |
| | | 2 | 24 | 63 | 38 |
| | | 3 | 4 | 22 | 16 |
| | | 4 | 0 | 0 | 9 |

TABLE 12

| | Example 22 | Example 23 |
|---|---|---|
| PC Resin (parts by weight) | 75 | 75 |
| ABS Resin (parts by weight) | 25 | 25 |
| Flame retardant | Flame retardant of Example 20 | Flame retardant of Example 21 |
| Flame retardant (parts by weight) | 15 | 15 |
| PTFE (parts by weight) | 0.3 | 0.3 |
| Heat distortion temp. (°C.) | 103 | 100 |
| Flame retardance Average burning time (sec.) | 1.8 | 1.7 |
| Dripping over flame | 0 | 0 |
| UL 94 | V-0 | V-0 |

What is claimed is:

1. A flame-retardant resin composition which comprises:
   100 parts by weight of a polycarbonate resin (A);
   0.1 to 30 parts by weight of one or more of organic phosphorus compounds (B) represented by the following formula (1):

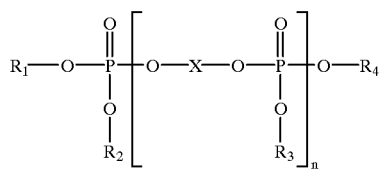

(1)

wherein X is

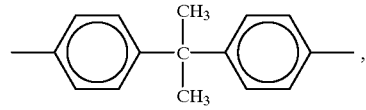

$R_1$, $R_2$, $R_3$ and $R_4$ independently represent a phenyl group or a xylyl group with at least one being a phenyl group and at least one being a xylyl group, and n is a positive integer; and 0.01–3 parts by weight of polytetrafluoroethylene.

2. A flame-retardant resin composition which comprises:
   100 parts by weight of a thermoplastic resin (A), wherein the thermoplastic resin (A) comprises 1–99 percent by weight of a polycarbonate resin and 99–1 percent by weight of a rubber reinforced resin which comprises a rubbery polymer and at least one vinyl compound;
   0.1 to 30 parts by weight of one or more of organic phosphorus compounds (B) represented by the following formula (1):

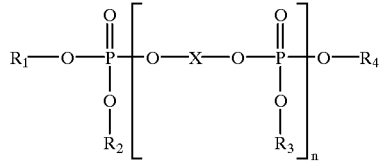

(1)

wherein X is
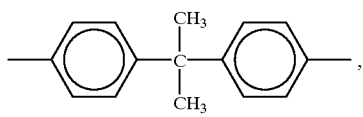
R$_1$, R$_2$, R$_3$ and R$_4$ independently represent a phenyl group or a xylyl group with at least one being a phenyl group and at least one being a xylyl group, and n is a positive integer; and
0.01–3 parts by weight of polytetrafluoroethylene.
* * * * *